United States Patent [19]
Lim et al.

[11] Patent Number: 5,865,854
[45] Date of Patent: Feb. 2, 1999

[54] BIS-(2-4-DIAMINOPHENOXY) BENZENES AND THEIR USE AS COUPLING COMPONENTS IN OXIDATIVE HAIR COLORING COMPOSITIONS AND METHODS

[75] Inventors: Mu-Iii Lim, Trumbull; Yuh-Guo Pan, Stamford; Linas R. Stasaitis, Fairfield, all of Conn.

[73] Assignee: Bristol-Myers Squibb Company, New York, N.Y.

[21] Appl. No.: 975,912

[22] Filed: Nov. 21, 1997

[51] Int. Cl.$^6$ .............................. A61K 7/13; C07C 217/90
[52] U.S. Cl. ......................... 8/408; 8/406; 8/411; 8/416; 8/649; 564/430
[58] Field of Search ................................. 8/405, 406, 408, 8/411, 416, 610, 649; 564/430

Primary Examiner—Paul Lieberman
Assistant Examiner—Caroline D. Liott
Attorney, Agent, or Firm—Charles J. Zeller

[57] ABSTRACT

The invention provides compositions and methods containing novel bis-(2,4-diaminophenoxy)benzene coupling compounds, and cosmetically acceptable salts thereof, for use with conventional primary intermediate dye compounds and oxidizing agents for the oxidative coloring of human hair. The compositions of the invention may also contain other components typically used in oxidative hair dye preparations to impart intense and lasting coloration to hair.

19 Claims, No Drawings

BIS-(2-4-DIAMINOPHENOXY) BENZENES AND THEIR USE AS COUPLING COMPONENTS IN OXIDATIVE HAIR COLORING COMPOSITIONS AND METHODS

FIELD OF THE INVENTION

The present invention relates generally to compositions of stable oxidative hair dyes that result in long-lasting and true color of the hair after application. The invention more particularly relates to novel bis-(2,4-diaminophenoxy) benzenes and their use as coupling components in oxidative hair dyes.

BACKGROUND OF THE INVENTION

Oxidative hair dye colorants are essential elements in hair dyeing preparations for the permanent dyeing of human hair. The hair dyeing process is achieved, in general, by the reaction of certain dye compounds (known as primary intermediates or primary dye intermediates) with certain coupling compounds in the presence of a suitable oxidizing agent or compound, such as hydrogen peroxide. Oxidative dyes are especially useful for their intense color formation and fastness to light and washing.

In order for procedures using permanent oxidative dyes to work properly, a number of parameters and conditions are important to consider in the use of these dyes in admixture with couplers in hair color preparations for human hair. Among these are the final color and color intensity that are produced after application to the subject's hair; the wash fastness and the light fastness of the resulting dye; the resistance of the dye to perspiration; the type of hair being dyed, e.g., virgin hair or waved hair; and the resistance of the dye to various hair treatments, such as permanent wave, straightening, shampooing, conditioning and rubbing. In addition, the dye must have virtually no allergenicity or dermal adverse reactions. Ideally, the dye product remains stable against the above-mentioned external influences and against chemical agents for a suitable period of time after application to the hair, for example, for at least four to six weeks. The dye-containing composition is economical to produce and has a reasonable shelf life. Further, the components of oxidative hair dye compositions should optimally produce the strongest possible color shades that correspond as closely as possible to the natural hair color nuances.

U.S. Pat. Nos. 4,371,370 and 4,314,809 to D. Rose et al. describe bis(2,4-diaminophenoxy) alkanols and bis(2,4-diaminophenoxy) alkanes, respectively, as coupling compounds in oxidative hair dyes. U.S. Pat. No. 5,114,429 to A. Junino et al. describes compounds consisting of N,N'-bis(β-hydroxyethyl)-N,N'-bis(4'-aminophenyl)-1,3-diamino-2-propanol and N,N'-bis(ethyl)-N,N'-bis(4'-amino-3'-methylphenyl)ethylenediamine for use in the dyeing of keratinous fibers, including human hair. German Patent Application No. DE 2,934,329 to Henkel describes binuclear analogs of 2,4-diaminoanisole for use as hair dyeing compounds. German Patent Application No. DE 3,235,615 describes bis(2,4-diaminophenyl) alkanes as couplers in hair dye compositions. In general, the primary intermediates and couplers described in these patents and published patent applications are linked by alkyl chains. Phenylalkyl-substituted primary intermediates and couplers are also described in the art. The types of primary intermediates and couplers disclosed in the art are benzene, pyridine and pyrimidine, pyrazolone, naphthalene, indole, indolinone or other heterocyclic rings containing electron-donating groups such as amino, alkylamine, hydroxyl, and alkoxy groups.

A continued need in the art is the discovery of hair dye components, including primary intermediates and couplers, that optimally satisfy all of the above-mentioned requirements and afford advantageous properties to the user. Until the compounds of the present invention, oxidative hair colorants having a phenyl group as a linker were not known or available to those having skill in the art. The structural features of the novel coupling compounds in accordance with the present invention provide two coupler units connected by a phenyl group as a linker, thereby producing coupling compounds that are larger than standard or commonly known human hair colorants and which provide intense and lasting coloration to hair. Indeed, that the compounds of the present invention are able to penetrate hair fibers to produce lasting colors of deep intensity in spite of their large molecular size is a surprising result to those having skill in the art.

SUMMARY OF THE INVENTION

It is an object of the present invention to provide oxidative hair dye compositions and methods comprising novel coupler compounds as components used in the oxidative coloring of human hair.

It is another object of the present invention to provide novel couplers of the class of bis-(2,4-diaminophenoxy) benzenes as components for use in oxidative hair colorants. In accordance with the present invention the novel compounds may be generally used in the dyeing of keratinous fibers, including but not limited to human hair.

It is yet another object of the present invention to provide compositions and methods for the oxidative coloration of human hair comprising novel coupling compounds that are bis-(2,4-diaminophenoxy) benzenes to impart intense coloration and fastness of color to the hair after application with conventional dye or primary intermediate compounds.

It is a further object of the present invention to provide a process for coloring human hair in which a novel coupling compound is employed.

It is yet a further object of the present invention to provide novel couplers that comprise two coupler units uniquely connected via a phenyl group as a linker. In accordance with the invention, such compounds impart an intense and long-lasting blue coloration to hair when used in admixture with at least one suitable conventional primary intermediate and/or with other coupling components.

Further objects and advantages afforded by the invention will be apparent from the detailed description hereinbelow.

DETAILED DESCRIPTION OF THE INVENTION

The present invention provides oxidative hair dye compositions and methods which include novel coupling compounds of the class of bis-(2,4-diaminophenoxy) benzenes. Such coupling compounds are unique, as no other oxidative hair coupling colorants having a phenyl group as a linker are known or available to those in the art.

The compounds of the invention have the following structural formulae I or II:

I:

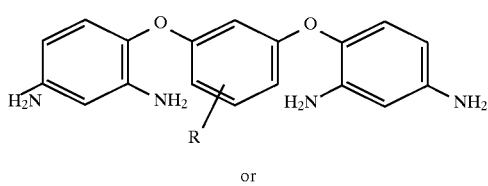

or

II:

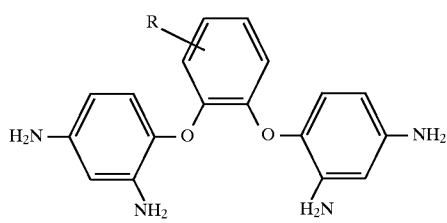

herein R=hydrogen (H) or halogen, wherein nonlimiting examples of suitable halogens are fluorine (F), chlorine (Cl) and bromine (Br); $C_1$–$C_5$ alkyl, including, for example, methyl, ethyl, propyl, isopropyl, butyl, isobutyl, pentyl, isopentyl and the like; $C_1$–$C_5$ monohydroxyalkyl; $C_1$–$C_5$ alkylamino; and amino groups, such as $NH_2$.

Preferred coupler compounds of Formula I are those as described in the examples where R is positioned between the two hydroxy groups on the center ring and in which R=H (defined as Compound 1 herein), $CH_3$ (defined as Compound 2 herein) or $NH_2$ (defined as Compound 3 herein).

A preferred coupler compound of formula II is Compound 4, wherein R=H, having the following structural formula:

Compound 4

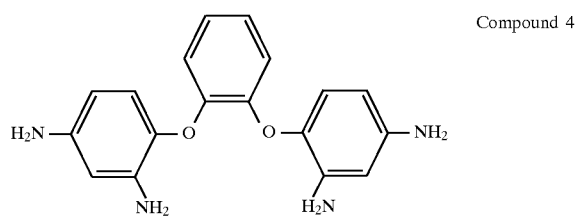

The novel compounds of the present invention, and cosmetically acceptable salts thereof, for example, inorganic or organic acids, serve as coupling components in the compositions of the invention. Examples of useful salts include, but are not limited to, chlorides, sulfates, phosphates, acetates, proprionates, phosphates, lactates, citrates and the like. The above-illustrated coupler compounds provided surprising results in that they impart intense coloration to hair despite the fact that these compounds are significantly larger than other, conventionally-used hair colorants. The large molecular size of the compounds of the present invention might be expected to have difficulty penetrating the hair fiber to couple with the other components of the dye compositions. However, these molecules were surprisingly found to function most effectively in their capacity as couplers to produce a very intense color, despite being larger than conventionally-used couplers.

An advantage afforded by the use of the coupler compounds of the present invention for coupling a primary intermediate, such as N,N-bis(2-hydroxyethyl)-p-phenylenediamine, is that the blue color obtained has a high degree of wash and light fastness when a tinctorially effective ratio of the primary intermediate and the novel coupler is used. By contrast, when the conventional coupler 1-naphthol was used for coupling the N,N-bis-(2-hydroxyethyl)-p-phenylenediamine primary intermediate, less wash and light fastness ensued. As is appreciated by those in the art, the combination of 1-naphthol and N,N-bis-(2-hydroxyethyl)-p-phenylenediamine is used to produce blue coloration in a number of commercial products.

In accordance with the present invention, Table 1 presents the total color changes after a 3 hour shampooing test. In Table 1, $\Delta E$ is defined as $\sqrt{(\Delta L)^2+(\Delta a)^2+(\Delta b)^2}$. As demonstrated in this table, the smaller the $\Delta E$ value, the better the wash fastness of a formulation containing the designated couplers and primary intermediates. For example, on gray hair, compounds 1 and 2 as defined herein have $\Delta E$ values of 2.53 and 1.17, respectively, while 1-naphthol, a conventional coupler and defined as compound 6 in Table 1, has a $\Delta E$ value of 4.98.

On bleached hair, the $\Delta E$ difference between the couplers of the present invention and 1-naphthol is striking and statistically significant. Specifically, the $\Delta E$ value of 1-naphthol is 15.12, while the $\Delta E$ values of compounds 1, 2 and 4 of the present invention range from 0.90 to 2.31. Photo fading studies at 72 hours (Table 1) have also shown that on both gray and bleached hair, the photo fading property of the couplers of the invention is much improved over that of 1-naphthol.

In Table 1, "L", "a", and "b" represent the Hunter values which measure the intensity and tonality of the color. As presented in this Example, the colors are evaluated utilizing the standard Hunter Tristimulus values. In the Hunter method, the parameters a and b may be positive or negative and define the chromatic condition of the hair. Thus, the more positive the a value, the greater the redness of the hair, while negative a values indicate greenness. Similarly, positive b values indicate yellowness, while negative b values indicate blueness. The L parameter is a measure of color intensity and has a value of 0 for absolute black to 100 for absolute white.

TABLE 1

Coupling of Dye Compound 5* With Novel Coupler Compounds 1, 2 and 4**
HUNTER VALUES

| Compound | | Standard | | | 3 Hour Wash Fastness | | | | | | | 72 Hour Photo Fading | | | | | | |
|---|---|---|---|---|---|---|---|---|---|---|---|---|---|---|---|---|---|---|
| | | L | a | b | L | a | b | $\Delta L$ | $\Delta a$ | $\Delta b$ | $\Delta E$ | L | a | b | $\Delta L$ | $\Delta a$ | $\Delta b$ | $\Delta E$ |
| 5 + 1 | Gray | 12.24 | 0.08 | -2.89 | 12.45 | 1.80 | -1.04 | -0.21 | -1.72 | -1.85 | 2.53 | 13.77 | 0.12 | 0.75 | -1.53 | -0.04 | -3.64 | 15.72 |
| (2:1) | Bleached | 10.84 | 0.11 | -0.34 | 10.93 | 1.00 | -0.31 | -0.09 | -0.89 | -0.03 | 0.90 | 11.41 | 0.35 | 0.14 | -0.57 | -0.24 | -0.48 | 12.33 |
| 5 + 2 | Gray | 11.78 | 0.31 | -2.69 | 12.29 | -0.74 | -2.80 | -0.51 | 1.05 | 0.11 | 1.17 | 13.75 | -0.56 | -0.55 | -1.97 | 0.87 | -2.14 | 12.83 |
| (2:1) | Bleached | 11.13 | 0.23 | -1.01 | 12.48 | -0.51 | -1.78 | -1.35 | 0.74 | 0.77 | 1.72 | 12.70 | -0.16 | 0.23 | -1.57 | 0.39 | -1.24 | 12.09 |
| 5 + 4 | Gray | 13.64 | 0.75 | -4.76 | 16.45 | -1.66 | -2.80 | -2.81 | 2.41 | -1.96 | 4.19 | 14.27 | -0.46 | 0.40 | -0.63 | 1.21 | -5.16 | 12.54 |

TABLE 1-continued

Coupling of Dye Compound 5* With Novel Coupler Compounds 1, 2 and 4**
HUNTER VALUES

| Compound | | Standard | | | 3 Hour Wash Fastness | | | | | | | 72 Hour Photo Fading | | | | | | |
| --- | --- | --- | --- | --- | --- | --- | --- | --- | --- | --- | --- | --- | --- | --- | --- | --- | --- | --- |
| | | L | a | b | L | a | b | ΔL | Δa | Δb | ΔE | L | a | b | ΔL | Δa | Δb | ΔE |
| (2:1) | Bleached | 11.10 | 0.39 | −0.75 | 13.24 | −0.45 | −0.57 | −2.14 | 0.84 | −0.18 | 2.31 | 12.96 | −0.38 | 0.46 | −1.86 | 0.77 | −1.21 | 12.26 |
| 5 + 6*** | Gray | 19.15 | 0.21 | −7.23 | 24.10 | −0.30 | −6.98 | −4.95 | 0.51 | −0.25 | 4.98 | 27.44 | −0.55 | 1.84 | −8.29 | 0.76 | −9.07 | 27.11 |
| (1:1) | Bleached | 12.13 | 2.63 | −7.93 | 23.82 | 0.09 | −17.18 | −11.69 | 2.54 | 9.25 | 15.12 | 15.49 | −0.40 | −3.89 | −3.36 | 3.03 | −4.04 | 24.95 |

*: Dye Compound 5 is bis(2-hydroxyethyl)-p-phenylenediamine.
**: Compounds 1, 2 and 4 are the novel couplers as depicted by the structural formulae hereinabove.
***: Coupler Compound 6 is 1-naphthol.

As described above, the large size of the dye coupler molecules provided by the present invention might be expected to preclude such molecules from being absorbed by the hair and providing intense coloration. However, and surprisingly, the color intensity afforded by the couplers of the present invention (see Table 1) is as strong as the conventional coupler 2,4-diaminoanisole, which is a much smaller molecule, as presented in Table 2. For example, on gray hair, the L value obtained from a formulation comprising N,N-bis-(2-hydroxyethyl)-p-phenylenediamine as primary intermediate and 2,4-diaminoanisole as coupler is 12.01 (see Table 2), while the L value obtained from a formulation comprising N,N-bis(2-hydroxyethyl)-p-phenylenediamine as the primary intermediate and compound 1 of the present invention as the coupler is 12.24 (see Table 1, Standard L value for Compounds 5+1). These results demonstrate that the diaminophenoxy benzenes of the present invention, which are large compared with the smaller-sized, conventional coupler molecules, unexpectedly produce virtually the same results for gray hair coloring.

TABLE 2

Coupling of N,N-bis(2-hydroxyethyl)-p-phenylenediamine
(Compound 5) with 2,4 diaminoanisole (Compound 7)

| COMPOUND | | HUNTER VALUES | | |
| --- | --- | --- | --- | --- |
| 5 + 7 | | L | a | b |
| | Gray | 12.01 | 0.91 | −3.54 |
| | Bleached | 11.01 | 0.68 | −0.51 |

Another advantage provided by the present invention is that the dye uptake of the novel coupler compounds is more evenly distributed between gray and bleached hair than the uptake by the conventional coupler compound, 1-naphthol. For example, when N,N-bis(2-hydroxyethyl)-p-phenylenediamine (compound 5) couples with 1-naphthol (compound 6), the L value on gray hair is 19.15 and the L value on bleached hair is 12.13. Such a difference in the L values between gray hair and bleached hair would be expected based on the knowledge among those having skill in the art. By contrast, in the case of dye compound 5 coupling with compound 2 of the present invention, the L value on gray hair is 11.78 and the L value on bleached hair is 11.13. The similarity of the L values between gray and bleached hair for the couplers of the present invention combined with the known primary intermediate (5) is a surprising result attributed to the present inventive discovery.

The hair dyeing compositions described herein contain, in addition to at least one of the novel bis-(2,4-diaminophenoxy) benzene coupling molecules encompassed by the present invention, at least one other known and usual primary intermediate component ingredient, and, optionally, other coupler compounds and conventional direct-acting colorants and dyes in admixture, should these substances be necessary or desired for the development and production of certain color nuances and tints.

Included among the primary intermediates and dye precursor components which may be considered for use in the dye compositions of the present invention are the following:

(1) p-Phenylenediamine derivatives such as p-Toluenediamine; p-Phenylenediamine; 2-Chloro-p-phenylenediamine; N-Phenyl-p-phenylenediamine; N-2-Methoxyethyl-p-phenylenediamine; N,N-Bis-hydroxyethyl-p-phenylenediamine; 2-Hydroxymethyl-p-phenylenediamine; 2-Hydroxyethyl-p-phenylenediamine; 4,4'-Diaminodiphenylamine; 2,6-Dimethyl-p-phenylenediamine; 2-iso-Propyl-p-phenylenediamine; N-(2-Hydroxypropyl)-p-phenylenediamine; 2-Propyl-p-phenylenediamine; 1,3-Bis-(N-hydroxyethyl)-N-(4-aminophenyl)amino)-2-propanol; and 2-Methyl-4-dimethylaminoaniline, or combinations thereof.

(2) p-Aminophenol derivatives such as p-Aminophenol; p-Methylaminophenol; 3-Methyl-p-aminophenol; 2-Hydroxymethyl-p-aminophenol; 2-Methyl-p-aminophenol; 2-(2'-Hydroxyethylaminomethyl)-p-aminophenol; 2-Methoxymethyl-p-aminophenol; and 5-Aminosalicylic acid, or combinations thereof.

(3) Ortho-Developers such as Catechol; Pyrogallol; o-Aminophenol; 2,4-Diaminophenol; 2,4,5-Trihydroxytoluene; 1,2,4-Trihydroxybenzene; 2-Ethylamino-p-cresol; 2,3-Dihydroxynaphthalene; 5-Methyl-o-aminophenol; 6-Methyl-o-aminophenol; and 2-Amino-5-acetaminophenol, or combinations thereof.

(4) Naphthols, phenols and resorcinol derivatives such as 2-methyl-1-naphthol; 1-acetoxy-2-methylnaphthalene; 1,7-Dihydroxynaphthalene; Resorcinol; 4-Chlororesorcinol; 1-Naphthol; 1,5-Dihydroxynaphthalene; 2,7-Dihydroxynaphthalene; 2-Methylresorcinol; 1-Hydroxy-6-aminonaphthalene-3-sulfonic acid; Thymol (2-isopropyl-5-methylphenol); 2-Chlororesorcinol; 2,3-Dihydroxy-1,4-naphthoquinone; and 1-Naphthol-4-sulfonic acid, or combinations thereof.

(5) m-Phenylenediamines such as m-Phenylenediamine; 2,4-Diaminophenoxyethanol; N,N-bis-hydroxyethyl-m-phenylenediamine; 2,6-Diaminotoluene; $N^2$-bis-Hydroxyethyl-2,4-diaminophenetole; Bis-(2,4-diaminophenoxy)-1,3-propane; 1-Hydroxyethyl-2,4-diaminobenzene; 2-Amino-4-hydroxyethylamino anisole; Aminoethyloxy-2,4-diaminobenzene; 2,4-Diaminophenoxyacetic acid; 4,6-Bis-hydroxyethyloxy-m-phenylenediamine; 2,4-Diamino-5-methylphenetole; 2,4-

Diamino-5-hydroxyethyloxytoluene; 2,4-Dimethoxy-1,3-diaminobenzene; and 2,6-Bis-hydroxyethylamino-toluene, or combinations thereof.

(6) m-Aminophenols such as m-Aminophenol; 2-Hydroxy-4-carbamoylmethylamino toluene; m-Carbamoylmethylamino phenol; 6-Hydroxybenzomorpholine; 2-Hydroxy-4-aminotoluene; 2-Hydroxy-4-hydroxyethylaminotoluene; 4,6-Dichloro-m-aminophenol; 2-Methyl-m-aminophenol; 2-Chloro-6-methyl-m-aminophenol; 2-Hydroxyethyloxy-5-aminophenol; 2-Chloro-5-trifluoroethylaminophenol; 4-Chloro-6-methyl-m-aminophenol; N-Cyclopentyl-3-aminophenol; N-Hydroxyethyl-4-methoxy-2-methyl-m-aminophenol; and 5-Amino-4-methoxy-2-methylphenol, or combinations thereof.

(7) Heterocyclic derivatives such as 2-Dimethylamino-5-aminopyridine; 2,4,5,6-Tetra-aminopyrimidine; 4,5-Diamino-1-methyl-pyrazole; 1-Phenyl-3-methyl-5-pyrazolone; 6-Methoxy-8-aminoquinoline; 2,6-Dihydroxy-4-methylpyridine; 5-Hydroxy-1,4-benzodioxane; 3,4-Methylenedioxyphenol; 4-Hydroxyethylamino-1,2-methylenedioxybenzene; 2,6-Dihydroxy-3,4-dimethylpyridine; 5-Chloro-2,3-dihydroxypyridine; 3,5-Diamino-2,6-dimethoxypyridine; 2-Hydroxyethylamino-6-methoxy-3-aminopyridine; 3,4-Methylenedioxyaniline; 2,6-Bis-hydroxyethyloxy-3,5-diaminopyridine; 4-Hydroxyindole; 3-Amino-5-hydroxy-2,6-dimethoxypyridine; 5,6-Dihydroxyindole; 7-Hydroxyindole; 5-Hydroxyindole; 2-Bromo-4,5-methylenedioxyphenol; 6-Hydroxyindole; Isatin (Indole-2,3-dione); 3-Amino-2-methylamino-6-methoxypyridine; 2-Amino-3-hydroxypyridine; 2, 6-Diaminopyridine; 5-(3,5-Diamino-2-pyridyloxy)-1,3-dihydroxypentane; 3-(3,5-Diamino-2-pyridyloxy)-2-hydroxypropanol; and 4-Hydroxy-2,5,6-triaminopyrimidine, or combinations thereof.

The bis-(2,4-diaminophenoxy) benzene coupling compounds of the invention are typically present in the novel hair dyeing compositions of the present invention in an amount of approximately 0.01 to 10%, by weight, preferably approximately 0.1 to 5%, by weight. The total quantity of oxidative colorant, consisting of dye substance(s) and coupling substance(s) will suitably amount to approximately 0.1 to 10%, by weight and preferably 0.5 to 5% by weight.

It is to be understood that, unless otherwise specified herein, all components of the compositions of the present invention are present in % by weight, based on the total weight of the composition.

In the compositions of the present invention, the coupling component is generally used in approximately equimolar quantities relative to the developing component. However, it will be appreciated that the dye component in relation to the coupler may be present either in increased or decreased amounts depending upon the formulation and the desired color, intensity or effect. As an example, the coupling and dye components can be present in a molar range of from about 2:1 to 1:2, with a 10% or less excess or deficiency being acceptable. In general terms, the dye component and the coupling component, or cosmetically acceptable salts thereof, will be in amounts effective for the tincturing of a hair fiber.

The hair dye preparations of the present invention may be formulated into cosmetic preparations such as a solution, cream, lotion, gel or emulsion. As an illustrative example, if formulated as a lotion, the compositions of the invention may contain organic solvents to assist in dissolving the dye precursors. Accordingly, the organic solvent content of the lotion may be from 0% to about 20%, preferably about 1% to 15%. Typically useful solvents include alcohols containing up to three carbon atoms such as ethanol and isopropanol, polyhydroxy alcohols such as propylene or hexylene glycol and lower alkyl ethers thereof such as ethoxy ethers.

In addition, the hair dyeing compositions in accordance with the present invention may optionally contain other conventionally-used adjuvants and cosmetic additives, or mixtures thereof, to achieve the final formulations. Examples of such additives include, but are not limited to, anti-oxidants, e.g., ascorbic acid, erythorbic acid, or sodium sulfite to inhibit premature oxidizing; oxidizing agents, fragrances and/or perfume oils; chelating agents; emulsifiers; coloring agents; thickeners; organic solvents; opacifying agents, dispersing agents, sequestering agents, hair-care substances; humectants; anti-microbials; and others. The list of optional ingredients is not intended as limiting. Other suitable adjuvants for inclusion in the hair dye compositions of the invention are disclosed, for example, in Zviak, *The Science of Hair Care* (1986) and in Balsam and Sagarin, *Cosmetics: Science and Technology*, Vol. 2, Second Edition, (1972).

Thickeners that may be used in the compositions of the present invention include a variety of fatty acid soaps and associative polymeric thickeners. The fatty acid soaps are alkaline metal salts or alkanolamine salts of fatty acids with $C_{10}$–$C_{16}$ alkyl side chains. The preferred fatty acids include oleic acid, myristic acid and lauric acid, which are generally present in the compositions of the invention at about 0.5% to 20%, preferably about 1% to 10%. Associative thickeners are polymers that can thicken solutions at low concentrations. Among the associative thickeners that are useful in the compositions of the present invention are acrylates copolymer (sold by Rohm and Haas under the trade name Aculyn-33), ceteareth-20 acrylates/steareth-20 methacrylate copolymer (sold by Rohm and Haas under the trade name Aculyn-22), acrylates/steareth-20 itaconate copolymer and acrylates/ceteth-20 itaconate copolymer. Another class of associative thickeners that is useful in the compositions of the present invention includes the copolymers of polyurethane and polyethylene glycol or polyetherurethanes. One such illustrative material is sold by Rohm and Haas under the trade name Aculyn-44. The associative polymeric thickeners are generally present in the compositions of the invention at about 0.1% to 10%, preferably about 0.5% to 5%.

The oxidative coupling, i.e., the development of the dye, can, in principle, be performed with atmospheric oxygen to produce the final color product on the hair. However, chemical oxidation agents are suitably and preferably used. A preferred oxidizing agent for use as a developer or developing agent with primary intermediates and the couplers of the invention is hydrogen peroxide, although other peroxides may be employed. These include, for example, urea peroxide, melamine peroxide, perborates and percarbonates such as sodium perborate or percarbonate. The concentration of peroxide in the developer may be from about 0.5% to about 40%, preferably about 0.5% to 30%. If the preferred hydrogen peroxide is employed, the concentration will typically be from about 0.5% to about 12%, preferably about 3% to 9%.

The compositions of the invention may include a typical anionic, cationic, nonionic or amphoteric surfactant.

The anionic surfactants include the variety of alkyl sulfates, alkylether sulfates, alkyl sulfonates, alkyl sulfosuccinates and N-acyl sarcosinates. The commonly-used anionic surfactants are sodium and ammonium lauryl sulfates, sodium and ammonium laurether sulfate and alpha olefin sulfonates. Anionic surfactants are generally present in the compositions of the present invention at about 0.1% to 15%, preferably about 0.5% to 10%.

The nonionic surfactants that can be used in the present invention include the wide variety of ethoxylated alcohols, nonoxynols, alkanolamides, alkyl stearates, alkyl palmitates and alkylpolyglucosides. Examples of the commonly-used nonionic surfactants are cetyl alcohol, stearyl alcohol, oleyl alcohol; the various types of ethoxylated alkylphenols; lauramide DEA; lauramide MEA; isopropyl palmitate, isopropyl stearate and decylpolyglucoside. Nonionic surfactants are generally present in the compositions of the present invention at about 0.1% to 15%, preferably about 0.5% to 10%, by weight, of the final composition.

The compositions in accordance with the present invention may also contain one or more quaternary ammonium compounds that provide hair conditioning effects. The quaternary ammonium compounds can be monomeric or polymeric quaternary ammonium compounds. Nonlimiting examples of such compounds include cetyltrimonium chloride, stearyl trimonium chloride, benzalkonium chloride, behentrimonium chloride and a variety of polyquaterniums. The quaternary ammonium compounds are generally present in the compositions of the present invention at about 0.1% to 10%, preferably 0.5% to 5%.

There are a large number of amphoteric surfactants that are suitable for use in the present invention, including, for example, the well-known betaines, sultaines, glycinates and propionates. The selection of the amphoteric surfactant or mixture of surfactants for use in the present compositions and methods is not critical. The amount of amphoteric surfactant in the compositions of the present invention is normally from about 0.5% to about 15%, preferably about 2% to 10%.

Depending on the final formulated preparation, the compositions in accordance with invention may be weakly acidic, neutral or alkaline. In particular, the pH of the prepared compositions can range from about 7 to 11. Preferred is a pH range of about 8 to 10. Any of a wide variety of alkaline reagents can be used to adjust the pH of the hair coloring compositions. Such alkaline reagents include ammonium hydroxide, potassium or calcium hydroxide, sodium or potassium carbonate, sodium phosphate, sodium silicate, guanidine hydroxide, or any one of the alkylamines or alkanolamines, for example, ethylamine, triethylamine, trihydroxymethylamino amine, ethanolamine, diethanolamine, aminomethyl propanol, aminomethyl propanediol and the like. The preferred alkaline reagents are ammonium hydroxide, sodium carbonate and ethanolamine. With the reagents listed above, the selected pH will generally be achieved if the composition contains from about 0.1% to 15%, preferably about 0.5% to 5%, by weight, of an alkaline reagent.

The application of the dyeing components is carried out by methods familiar to those in the art, for example, by mixing the hair dyeing preparation with an oxidant shortly before use, or at the time of applying the mixture onto the hair. On the hair, the compositions form a stable formulation with enough consistency and body to remain on the hair during the complete coloring period without dripping or running. The primary intermediate and coupler, i.e. the dye precursors, diffuse rapidly into the hair together with the oxidizing agent, or developer. The dyes form within the hair fiber, and since they are large molecules, remain in the hair so that the color change is permanent. The term "permanent" means the dye does not readily wash out of the hair with ordinary shampoos. At the end of coloring application (e.g., approximately 5 to 45 minutes, preferably approximately 30 minutes), the hair is washed with an ordinary water rinse followed by a shampoo. The application temperature is in the range of about 15° C. to 50° C.

Those in the art will appreciate that the compositions and methods of the present invention are appropriate for the dyeing of keratinous fibers, including the hair fibers of animals and humans, with particular application to the oxidative coloring of human hair.

As mentioned above, the hair dyeing compounds in accordance with the invention produce particularly intense color, particularly the blue shades. The colors obtained provide strong fastness to light, shampooing and washing, rubbing and abrasion.

The compositions of this invention may be separately provided in a kit or packaged form ready for mixing by the user, either professional or personal, to initiate the dyeing process. The kit provided in accordance with this invention comprises containers for housing the developer and the dye precursors. In the most convenient form, there will be two containers, one containing the dye precursors, e.g., as a lotion; the other containing the oxidizing agent.

The method of the invention comprises applying a mixture of the dye precursors, and other additives if necessary or desired, to the hair to be colored and allowing the resultant composition mixture to remain in contact with the hair until the desired hair color has been attained, after which time the composition is removed from the hair as conventionally known.

EXAMPLES

The examples as set forth herein are meant to exemplify the various aspects of carrying out the invention and are not intended to limit the invention in any way.

Example 1

The bis-(2,4-diaminophenoxy) benzenes of the present invention can be prepared as described in this example. In general, the synthesis of the novel couplers requires two steps involving aromatic nucleophilic substitution and catalytic hydrogenation. For example, reaction of resorcinol (compound 8) with two equivalents of 2,4-dinitrofluorobenzene (compound 9) in the presence of potassium fluoride or potassium carbonate in dimethylformamide (DMF) produces the tetranitro derivative (compound 10) which is converted into the coupler compound 1 presented hereinabove.

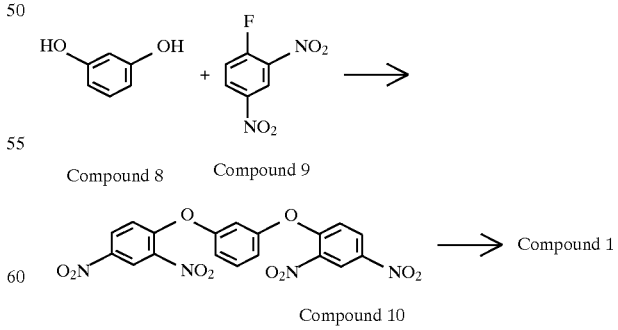

Preparation of Compound 10

A mixture of resorcinol (compound 8) (5 g, 45.4 mmole) and 2,4-dinitrofluorobenzene (compound 9) (17.75 g, 95.4 mmole) in DMF (100 mL) in the presence of potassium carbonate (13.2 g, 95.5 mmole) was stirred at 100° C. for two hours and poured into a slurry of crushed ice. The resulting precipitate was collected, washed three times with cold water and air-dried to yield compound 10 (19.87 g): mp 189.6°–190.5° C.; $^{1}$HNMR (300 MHz, DMSO-$d_6$) δ 7.25 (dd, 2H, J=9.0, 2.1 Hz), 7.30 (t, 1H, J=2.1 Hz), 7.34 (d, 2H, J=9.0 Hz), 7.65 (t, 1H, J=8.1 Hz), 8.45 (dd, 2H, J=9.0, 2.7 Hz), 8.87 (d, 2H, J=2.7 Hz); MS m/z 442 (M$^+$).

Preparation of Compound 1

A suspension of compound 10 (10 g, 22.6 mmole) and 10% Pd/C (1 g) in ethyl acetate and methanol (150:20 mL) was hydrogenated at 60 psi for 1.5 hours. The mixture was filtered over a layer of Celite and washed with ethyl acetate (2 times, 20 mL). The combined filtrate was evaporated under reduced pressure to leave reddish syrup which, upon addition of methanol, crystallized to yield a white powder, compound 1 (7.0 g): mp 180° C.; $^{1}$HNMR (300 MHz, DMSO-$d_6$) δ 4.49 (s, 4H), 4.68 (s, 4H), 5.80 (dd, 2H, J=8.4, 2.1 Hz), 5.99 (d, 2H, J=2.1 Hz), 6.32– 6.37 (m, 3H), 6.49 (d, 2H, J=8.4 Hz), 7.07 (t, 1H, J=8.1 Hz): MS m/z 322 (M$^+$).

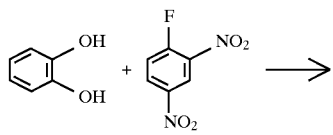

Compound 11  Compound 9

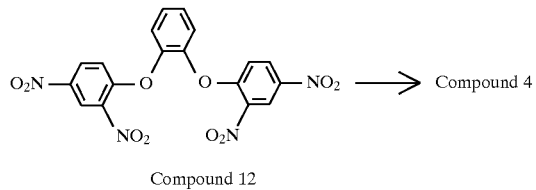

Compound 12

Preparation of Compound 12

A mixture of catechol (compound 11) (11.01 g, 100 mmole) and 2,4-dinitrofluorobenzene (compound 9) (37.22, 200 mmole) in DMF (200 mL) in the presence of potassium fluoride (11.62 g, 200 mmole) was stirred at 100° C. for 2 hours. The reaction mixture was poured into a slurry of crushed ice and water. The resulting precipitate was collected, washed with water, and air-dried to yield the compound 12 (42.81 g); mp 135°–136° C.: $^{1}$HNMR (300 MHz, DMSO-$d_6$) δ 7.18 (d, 2H, J=9.0 Hz), 7.53–7.62 (m, 4H), 8.41 (d, 2H, J=9.0 Hz), 8.78 (d, 2H, J=3.0 Hz); MS m/z 442 (M$^+$).

Preparation of Compound 4

The reduction of compound 12 (44.24 g, 100 mmole) was performed with 4.42 g of 10% Pd/C, 200 ml ethanol and 60 psi hydrogen on a Parr apparatus for 1.5 hours. The catalyst was filtered over a pad of Celite. The filtrate was acidified with 1 equivalent of concentrated sulfuric acid (10.21 g). The resulting precipitate was filtered and air-dried to afford 27.00 g of the tetra-amino product: mp 116°–118° C.; δ 4.6 (s, 4H), 4.64 (s, 4H), 5.79 (dd, 2H, J=8.4, 2.4 Hz), 6.01 (d, 2H, J=2.4 Hz), 6.50 (d, 2H, J=8.4 Hz), 6.62 (m, 2H), 6.80 (m, 2H); MS m/z 322 (M$^+$).

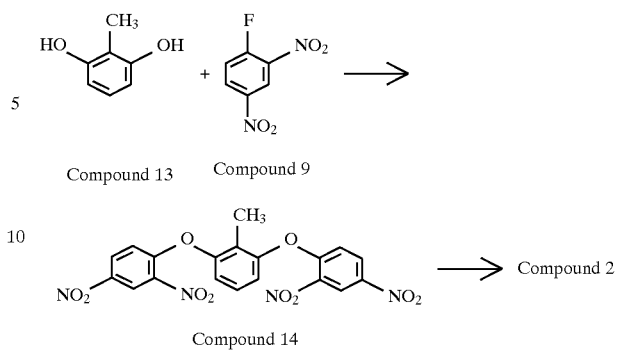

Compound 13  Compound 9

Compound 14

Preparation of Compound 14

A mixture of 2-methylresorcinol (compound 13) (12.41 g, 100 mmole), 2,4-dinitrofluorobenzene (compound 9) (37.2 g, 200 mmole) and potassium carbonate (27.64 g, 200 mmole) in DMF (100 mL) was stirred at 100° C. for 0.5 hour. The reaction mixture was poured into slurry of crushed ice and water. The resulting precipitate was collected, washed with water, and air-dried to yield compound 14 (45.67 g): mp 199°–201° C.; $^{1}$HNMR (300 MHz, DMSO-$d_6$) δ 2.00 (s, 3H), 7.20 (d, 2H, J=9.3 Hz), 7.26 (d, 2H, J=8.1 Hz), 7.50 (t, 1H, J=8.1 Hz), 8.42 (dd, 2H, J=9.3, 2.7 Hz), 8.91 (d, 2H, J=2.7 Hz); MS m/z 456 (M$^+$).

Preparation of Compound 2

A suspension of compound 14 (22.82 g, 50 mmole) and 10% Pd/C (2.3 g) in ethanol (150 mL) was hydrogenated at 60 psi hydrogen pressure for 1.5 hours. The product precipitated out during reduction. Therefore, glacial acetic acid (100 mL) was added and the reaction mixture was filtered over a pad of Celite. The filtrate was diluted with water and neutralized with potassium carbonate. The precipitate was collected, washed with water, and air-dried to yield compound 2 (14.66 g): mp 184° C.; $^{1}$HNMR (300 MHz, DMSO-$d_6$) δ 2.24 (s, 3H), 4.49 (s, 4H), 4.65 (s, 4H), 5.79 (dd, 2H, J=8.4, 2.1 Hz), 6.01 (d, 2H, J=2.1 Hz), 6.14 (d, 2H, J=8.4 Hz), 8.44 (d, 2H, J=8.4 Hz), 8.83 (t, 1H, J=8.4 Hz); MS m/z 336 (M$^+$).

Example 2

Hair dyeing compositions were prepared in accordance with the invention in the form of a lotion. An illustrative composition of the present invention is presented in Table 3:

TABLE 3

| Ingredient | Amount (g) |
| --- | --- |
| N,N-bis(2-hydroxyethyl)-p-phenylenediamine | 0.588 |
| Coupler 1 | 0.322 |
| Cocamidopropyl betaine | 2.000 |
| Ethylene glycol monoethylether | 1.000 |
| Benzyl alcohol | 1.000 |
| Monoethanolamine | 0.500 |
| Sodium sulfite | 0.020 |
| EDTA | 0.020 |
| Ascorbic Acid | 0.040 |
| Water | QS |
| Total | 10.000 |

The composition was used to dye swatches of blended gray and bleached human hair. The hair was soaked in the illustrative dye composition of the invention plus 20 volumes hydrogen peroxide (10.0 g) for 30 minutes at room temperature, and then rinsed with water, shampooed, and dried. The hair swatches were dyed a blue-black color having deep nuances and color fastness.

Example 3

As presented in Table 4, the novel coupler 4 of the present invention also coupled with the primary dye intermediate p-phenylenediamine (Compound 15) to color hair black under the conditions described above.

TABLE 4

Coupling of p-phenylenediamine (Compound 15) with Coupler Compound 4 of the Present Invention

| Compound | | HUNTER VALUES | | |
| --- | --- | --- | --- | --- |
| | | L | a | b |
| 15 + 4 (2:1) | Gray | 11.53 | 0.46 | −0.53 |
| | Bleached | 11.07 | 0.26 | −0.03 |

As various changes can be made in the above-described subject matter without departing from the scope and spirit of the invention, it is intended that all subject matter contained in the above description, shown in the accompanying drawings, or defined in the appended claims be interpreted as descriptive and illustrative, and not in a limiting sense. Many modifications and variations of the present invention are possible in light of the above teachings.

What is claimed is:

1. A compound of the formula I or II:

I: 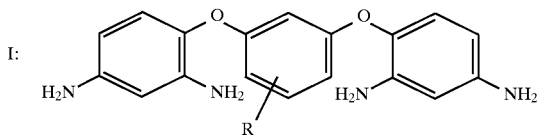

or

II: 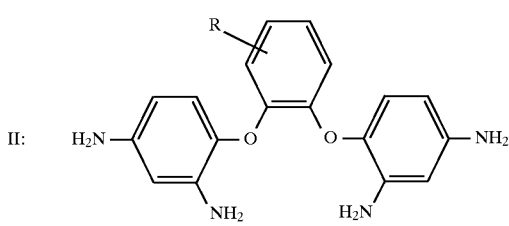

or a cosmetically acceptable salt thereof, wherein R is selected from the group consisting of halogen; $C_1$–$C_5$ monohydroxyalkyl; $C_1$–$C_5$ alkyl; $NH_2$; and $C_1$–$C_5$ alkylamino.

2. The compound according to claim 1, wherein R is selected from the group consisting of fluorine (F), chlorine (Cl) and bromine (Br).

3. The compound according to claim 2, wherein R is chlorine.

4. The compound according to claim 1, wherein R is selected from the group consisting of methyl, ethyl, propyl, isopropyl, butyl, isobutyl, pentyl and isopentyl.

5. The compound according to claim 4, wherein R is methyl.

6. The compound according to claim 1, wherein R is $NH_2$.

7. A composition for the oxidative coloring of human hair comprising a tinctorially effective amount of at least one coupling compound and at least one oxidative primary dye intermediate compound, or cosmetically acceptable salts thereof, said at least one coupling compound having the formula I or II:

I: 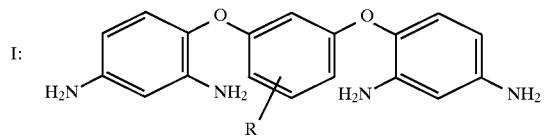

or

II: 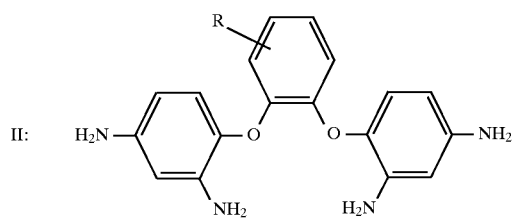

or a cosmetically acceptable salt thereof, wherein R is selected from the group consisting of H; halogen; $C_1$–$C_5$ monohydroxyalkyl; $C_1$–$C_5$ alkyl; $NH_2$; and $C_1$–$C_5$ alkylamino.

8. The composition according to claim 7, wherein the primary dye intermediate is selected from the group consisting of p-phenylenediamines and cosmetically acceptable derivatives thereof; p-aminophenols and cosmetically acceptable derivatives thereof; ortho-developers and cosmetically acceptable derivatives thereof.

9. The composition according to claim 8, further comprising conventional additives selected from the group consisting of other dye couplers, oxidizing agents, antioxidants, fragrances, perfume oils, chelating agents, emulsifiers, coloring agents, dispersing agents, opacifying agents, thickeners, organic solvents, surfactants, humectants and anti-microbials.

10. The composition according to claim 9, wherein the oxidizing agent is selected from the group consisting of hydrogen peroxide, urea peroxide, melamine peroxide, sodium perborate and sodium percarbonate.

11. The composition according to claim 10, wherein the oxidizing agent is present in the composition in an amount of about 5 to 30%, by weight.

12. The composition according to claim 8, wherein the coupling compound is present in the composition in an amount of about 0.01 to about 10%, by weight.

13. The composition according to claim 7, wherein the coupling compound and the primary dye intermediate are present in a molar ratio of from about 2:1 to 1:2.

14. A method for the oxidative coloring of human hair comprising contacting the hair with a hair coloring effective amount of the composition according to claim 8; and maintaining contact with the hair until the hair is permanently colored.

15. The method according to claim 14, further comprising contacting the hair with an oxidizing agent.

16. The method according to claim 15, wherein the oxidizing agent is present in the composition in an amount of about 5 to 30%, by weight.

17. The method according to claim 14, wherein the coupling compound is present in the composition in an amount of about 0.01 to about 10%, by weight.

18. The method according to claim 14, wherein the coupling compound and the primary dye intermediate are present in a molar ratio of from about 2:1 to 1:2.

19. The method according to claim 14, wherein said contact is maintained for about 5 to about 45 minutes, followed by rinsing the hair with water and, optionally, followed by shampooing.

* * * * *